(12) United States Patent
Sablone

(10) Patent No.: US 9,056,030 B2
(45) Date of Patent: Jun. 16, 2015

(54) SANITARY ARTICLE WEARABLE AS PANTS

(75) Inventor: Gabriele Sablone, Montesilvano (IT)

(73) Assignee: FAMECCANICA.DATA S.P.A., Sambuceto di San Giovanni Teatino (IT)

( * ) Notice: Subject to any disclaimer, the term of this patent is extended or adjusted under 35 U.S.C. 154(b) by 479 days.

(21) Appl. No.: 12/990,552

(22) PCT Filed: Apr. 24, 2009

(86) PCT No.: PCT/IB2009/051695
§ 371 (c)(1),
(2), (4) Date: Nov. 1, 2010

(87) PCT Pub. No.: WO2009/136308
PCT Pub. Date: Nov. 12, 2009

(65) Prior Publication Data
US 2011/0046594 A1    Feb. 24, 2011

(30) Foreign Application Priority Data

May 5, 2008 (IT) .............................. TO2008A0331

(51) Int. Cl.
*A61F 13/515* (2006.01)
*A61F 13/49* (2006.01)
*A61F 13/56* (2006.01)

(52) U.S. Cl.
CPC ......... *A61F 13/49015* (2013.01); *A61F 13/515* (2013.01); *A61F 13/5622* (2013.01)

(58) Field of Classification Search
CPC ............ A61F 13/5622; A61F 13/5633; A61F 2013/16
USPC ............. 604/389, 385.01, 385.04; 156/60, 66
See application file for complete search history.

(56) References Cited

U.S. PATENT DOCUMENTS 4,568,344 A * 2/1986 Suzuki et al. ................. 604/389
5,064,489 A * 11/1991 Ujimoto et al. ............... 156/164

(Continued)

FOREIGN PATENT DOCUMENTS

| CN | 1140985 A | 1/1997 |
|---|---|---|
| JP | H11-506037 A | 6/1999 |
| JP | 2003-508095 A | 3/2003 |

(Continued)

OTHER PUBLICATIONS

Dec. 7, 2009 International Search Report and Written Opinion in PCT Application No. PCT/IB2009/051695 (14 pages).

(Continued)

*Primary Examiner* — Tan-Uyen (Jackie) T Ho
*Assistant Examiner* — Peter S Vasat
(74) *Attorney, Agent, or Firm* — Popovich, Wiles & O'Connell, P.A.

(57) ABSTRACT

A sanitary article wearable as pants comprises a body or chassis 12 with a topsheet 13, a backsheet 14 and an absorbent core 15 interposed between the topsheet 13 and the backsheet 14. The article 10 has opposite extremities provided with closing side panels 16 extending laterally starting from at least one of said opposite extremities. The side panels 16 have proximal margins 160 connected to the body 12 in positions interposed between the topsheet 13 and the backsheet 14. In particular, the above-said proximal margins 160 of the side panels 16 are connected by thermal welding or ultrasound welding 170 to the topsheet 13 and adhesively 190 to the backsheet 14.

6 Claims, 1 Drawing Sheet

(56) References Cited

Figure 1:
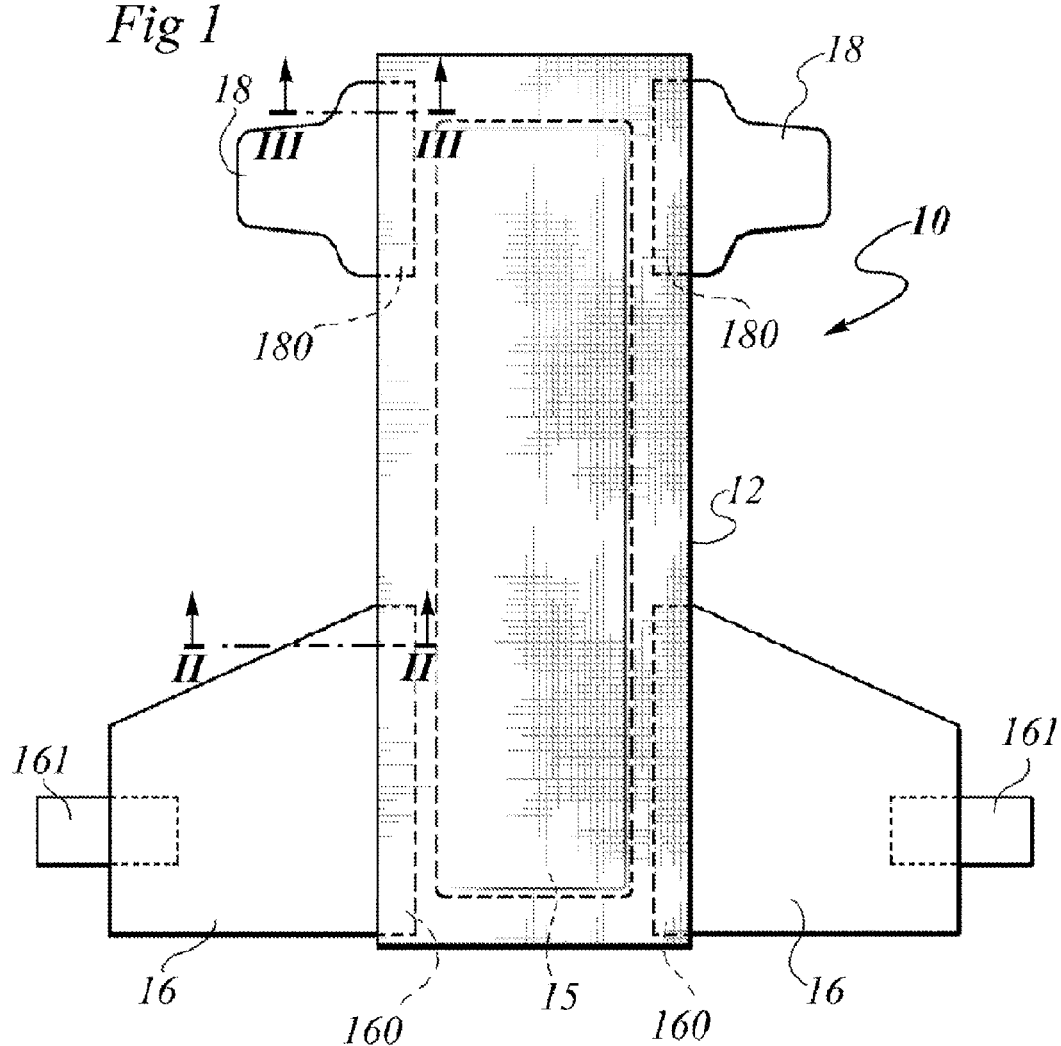

U.S. PATENT DOCUMENTS 5,997,521 A    12/1999    Robles et al.
6,605,070 B2    8/2003    Ludwig et al.

FOREIGN PATENT DOCUMENTS

| WO | WO 95/13775 A1 | 5/1995 |
| WO | WO 97/32552 A1 | 9/1997 |
| WO | WO 00/37005 A2 | 6/2000 |
| WO | WO 01/91666 A2 | 12/2001 |
| WO | WO 01/92013 A1 | 12/2001 |

OTHER PUBLICATIONS

Abstract for JP H11-506037 A (1 page).
Abstract for JP 2003-508095 A (1 page).
Abstract for CN 1140985 A (2 pages).

\* cited by examiner

SANITARY ARTICLE WEARABLE AS PANTS

FIELD OF THE INVENTION

The present description refers to sanitary products wearable as pants.

DESCRIPTION OF THE RELATED ART

Sanitary products wearable as pants have been available for many years in a wide range of manufactured forms.

A manufacturing solution particularly appreciated in recent years envisions that the diaper have a main body or chassis, to be wrapped concave around the crotch portion of the user, while the side panels protruding from the sides of one or both of the opposite extremities of the chassis allow closure of the article around the waistline of the user.

The main body or chassis has a layered structure in which are normally recognisable (in addition to various other accessory elements):

an upper layer or topsheet permeable to the evacuated body liquids, intended to face toward the body of the user;

a lower layer or backsheet impermeable to the body liquids intended to face toward the outside, that is, in the opposite position with respect to the body of the user; and an absorbent mat or core interposed between the topsheet and the backsheet.

A sanitary product corresponding to such morphology is known, for example, from the document WO-A-97/032552, taken as a model for the preamble of claim 1.

In particular, concerning the ways of connecting the side panels to the body or chassis of the article, the above cited document mentions the possibility of:

connecting the proximal margin of the panel to the topsheet, backsheet or both;

arranging the above-said proximal margin on the outer surface of the backsheet, on the inner surface of the topsheet or between the topsheet and the backsheet; and resorting to any fixing means known in the art, such as, for example, adhesives, thermal welding, pressure welding, ultrasound welding or any combination thereof.

In selecting a completely satisfying solution from among these acceptable possibilities for connecting the side panels to the body or chassis of the article, it is necessary to meet the needs deriving from the characteristics of the finished product (in particular guaranteeing a solid connection of the side panel to the body or chassis, avoiding undesired detachment and/or tearing phenomena), as well as needs of a strictly productive nature, for example, in terms of simplifying equipment and reducing costs.

More recently, in addition to these needs, an increased attention to issues of environmental protection have been added, linked both to the productive cycle of the article and the disposal of the same after use: in fact, the articles in question substantially qualify as single-use or disposable articles. In particular, the above-said environmental issues tend to look increasingly unfavourably on resorting to adhesives and glues and, particularly, to scarcely biodegradable adhesives.

OBJECT AND SUMMARY OF THE INVENTION

Thus, the invention has the object of providing a sanitary article that, on one hand, is able to suitably respond to the functional needs linked to its use and, on the other hand, can be produced and disposed of with reduced environmental impact.

The present invention has the object of providing a solution to such needs.

According to the present invention, such object is achieved my means of a sanitary article having the characteristics specifically recalled in the claims that follow.

The claims form an integral part of the technical disclosure provided herein relative to the invention.

BRIEF DESCRIPTION OF THE ANNEXED DRAWINGS

Figure 2:
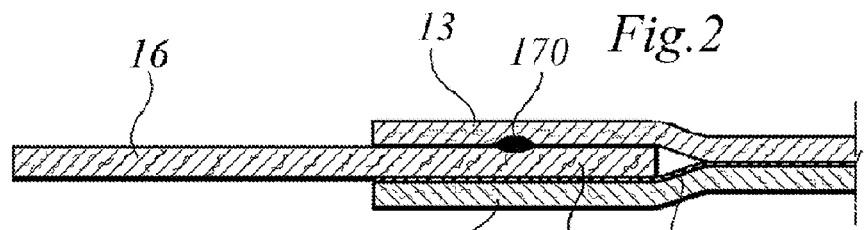
Figure 3:
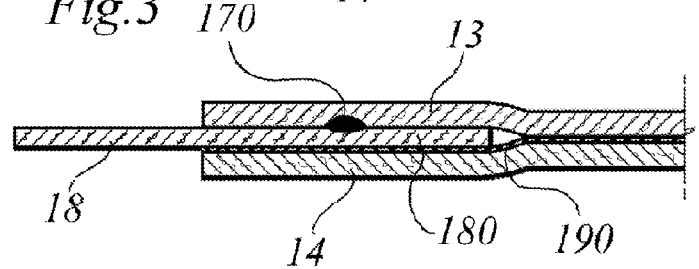

The invention will now be described, by way of non limiting example only, with reference to the annexed drawings, wherein:

FIG. 1 is a general schematic view of a sanitary article of the type described herein, illustrated in extended position, and FIGS. 2 and 3 are two views in section along the lines II-II and in FIG. 1.

DETAILED DESCRIPTION OF EMBODIMENTS

In the description that follows various specific details are illustrated aimed at a thorough understanding of the embodiments. The embodiments can be practiced without one or more of the specific details or with other methods, components, materials, etc. In other instances, known structures, materials or operations are not shown or described in detail to avoid obscuring the various aspects of the embodiments.

Reference throughout this specification to "one embodiment" or "an embodiment" means that a particular feature, structure or characteristic described in connection with the embodiment is included in at least one embodiment. Thus, the appearance of the phrases "in one embodiment" or in "an embodiment" in various places throughout this specification do not necessarily refer to the same embodiment. Furthermore, the particular features, structures or characteristics may be combined in any suitable manner in one or more embodiments.

The headings provided herein are provided for convenience only and thus do not interpret the field of protection or the scope of the embodiments.

In FIG. 1 the reference numeral 10 indicates a sanitary product wearable as pants in its entirety, illustrated herein in a flat, extended position. In the example illustrated herein, it is a conventional article (baby diaper, or adult incontinence product) intended to be sold open and to be closed pants-like after being placed on the body of the user. However, the solution described herein is susceptible of being applied also to the articles currently denominated "training pants" intended to be sold already closed in the pants configuration and to be pulled onto the body of the user.

Essentially, the product 10 is composed of a central body 12 destined to have a general U-conformation conferred thereto and be applied on the body of the user, wrapping it around the crotch portion of the user.

The body or chassis 12 has a structure wherein are usually recognisable (in addition to various other accessory elements):

an upper layer or topsheet 13 permeable to the evacuated body liquids, intended to face toward the body of the user;

a lower layer or backsheet 14 impermeable to the body liquids, intended to face toward the outside, that is, in the opposite position with respect to the body of the user; and an absorbent mat or core 15 interposed between the topsheet 13 and the backsheet 14.

Elastic side panels are also present, indicated with the references 16, extending from the central body 12, and allowing closure of the article (for example, by means of adhesive tabs 161 or micro hooks) around the waistline as worn by the user.

The side panels or inserts 16 are susceptible of being realised according to criteria better described in documents W-A-01/91666 and W-A-01/92013; also concerning the possibility of conferring characteristics of "breathability" to the panels 16, through the formation of transpiration openings.

The side panels can be present at both extremities (front and rear) of the central body 12. This is usually the case in articles of the training pants type, where the distal edges of the various panels are sealed together to provide the article as sold, with the closed conformation. It should be pointed out that the indications "front" and "rear" are used herein only to distinguish the two extremities and therefore have no specific relevance concerning the way in which the product is eventually worn.

The embodiment illustrated herein refers to the case (more frequent in the products sold "open") wherein the side panels 16 are at the rear extremity of the central body 12, while the two wings 18 protrude laterally from the front extremity of the central body 12, providing the article 10 (ideally seen in open and extended position, as represented in FIG. 1) with the typical hourglass conformation.

The representation in FIG. 1 is schematic in nature and is intended to highlight the fact that the solution described herein is susceptible of being applied to a wide variety of possible types of embodiments of the article 10.

For a more detailed illustration of additional characteristics of the article 10 (for example, concerning the presence of shaped edges delineating the contour of the openings for the legs of the user and also the presence of so-called cuffs or elastic edges arranged along the sides of the absorbent nucleus 15 functioning to containing laterally the bodily fluxes the reader is directed to the broad existing literature on the topic; this also regarding the choice of possible materials constituting the various parts of the article 10.

As is better appreciable in the views in section in FIGS. 2 and 3, both for the connection of the side panels 16, and for the connection of the front wings 18, the solution described herein envisions that the corresponding proximal margins, indicated with 160 and 180, respectively, are connected to the body or chassis of the article 10 interposing them sandwich-like between the topsheet 13 and the backsheet 14 of the body 12 of the article with the following ways of connecting:

thermal welding or ultrasound welding connection, along a welding line 170 (continuous or, preferably discontinuous) to the topsheet, and adhesive connection to the backsheet 14 exploiting the reduced layer of glue 190 normally already envisioned as so-called "construction glue" to keep the topsheet 13 and the backsheet 14 connected together on at least part of the external region with respect to the absorbent nucleus or core 15.

The experiments performed by the Applicant demonstrated that, surprisingly, such specific way of connecting is able—on one hand—to provide a solid connection of the side panels 16 (and of the side wings 18) to the body 12 of the article 10 without risk of accidental detachment or tearing, while—on the other hand—minimising recourse to adhesive layers (or glue).

Without limitation to any specific theory on this matter, the Applicant has reason to believe that the two connecting structures (thermal welding or ultrasound welding line 170, layer of glue 190) cooperate synergistically based on a mechanism wherein the adhesive connection realised by the layer of glue 190 maintains all three layers of the sandwich structure (topsheet 13, proximal margin 160 or 180, backsheet 14) in a condition of coherent co-planarity.

In this way it is possible to act so that the proximal margin 160 of the side panel 16 remains aligned with the general laying plane of the topsheet 13, so that traction efforts exerted on the side panel 16 during the use of the article 10 are transferred from the proximal margin 160 of the panel 16 to the topsheet 13 only as shear stresses acting in the common laying plane, that is, under conditions in which the thermal welding line 170 is able to exert the maximal connecting and retaining action.

Naturally, without prejudice to the underlying principle of the invention, the details of realisation and the embodiments may vary, even appreciably, with reference to what has been described herein by way of non-limiting example only, without departing from the scope of the invention as defined in the annexed claims.

The invention claimed is:

1. A sanitary article wearable as pants comprising:
a body or chassis including a topsheet being permeable to evacuated body liquids, a backsheet being impermeable to the body liquids, an adhesive connection layer between said topsheet and said backsheet, and an absorbent core interposed between said topsheet and said backsheet, said adhesive connection layer being applied to connect said topsheet to said backsheet at a first region surrounding said absorbent core, the body having opposite extremities; and
side panels extending laterally from at least one of said opposite extremities of said body, said side panels having proximal margins connected to said body at a second region interposed between said topsheet and said backsheet, said proximal margins having a first surface and a second opposing surface, said adhesive connection layer being sized to extend from said first region into said second region at which said proximal margins of said side panels are connected, said first surface of said proximal margins of said side panels being connected at said second region by thermal welding or ultrasound welding to said topsheet and said second opposing surface of said proximal margins of said side panels being connected at said second region adhesively to said backsheet by means of said adhesive connection layer.

2. The sanitary article according to claim 1, wherein said proximal margins of said side panels are connected to said topsheet by means of a discontinuous thermal welding or ultrasound welding line.

3. The sanitary article according to claim 1, wherein said proximal margins of said side panels are connected to said topsheet by means of a continuous thermal welding or ultrasound welding line.

4. The sanitary article according to claim 1, wherein said side panels comprise a pair of side panels extending laterally from one of said opposite extremities of said body and wherein the sanitary article further comprises a pair of side wings extending laterally from the other of said opposite extremities of said body, said side wings having proximal margins connected to said body in a position interposed between said topsheet and said backsheet, said adhesive connection layer being sized to extend to said position at which said proximal margins of said side wings are connected, said proximal margins of said side wings being connected by thermal welding or ultrasound welding to said topsheet and being connected adhesively to said backsheet by means of said adhesive connection layer.

5. The sanitary article according to claim 4, wherein said proximal margins of said side panels and said side wings are connected to said topsheet by means of a discontinuous thermal welding or ultrasound welding line.

6. The sanitary article according to claim 4, wherein said proximal margins of said side panels and said side wings are connected to said topsheet by means of a continuous thermal welding or ultrasound welding line.

\* \* \* \* \*